United States Patent
Kahle et al.

(10) Patent No.: US 11,433,017 B2
(45) Date of Patent: Sep. 6, 2022

(54) PROCESS FOR PRODUCING A WAX PREPARATION

(71) Applicant: SCHWAN-STABILO COSMETICS GMBH & CO. KG, Heroldsberg (DE)

(72) Inventors: Ingolf Kahle, Rückersdorf (DE); Simona Lebok, Nuremberg (DE); Christian Sprogar, Bubenreuth (DE)

( * ) Notice: Subject to any disclaimer, the term of this patent is extended or adjusted under 35 U.S.C. 154(b) by 185 days.

(21) Appl. No.: 16/473,556

(22) PCT Filed: Dec. 28, 2017

(86) PCT No.: PCT/EP2017/084769
§ 371 (c)(1),
(2) Date: Jun. 25, 2019

(87) PCT Pub. No.: WO2018/122348
PCT Pub. Date: Jul. 5, 2018

(65) Prior Publication Data
US 2020/0138696 A1 May 7, 2020

(30) Foreign Application Priority Data

Dec. 28, 2016 (DE) .................... 202016008030.0

(51) Int. Cl.
| | | |
|---|---|---|
| *A61Q 1/10* | (2006.01) | |
| *A61K 8/92* | (2006.01) | |
| *A61K 8/06* | (2006.01) | |
| *A61K 8/31* | (2006.01) | |
| *A61K 8/37* | (2006.01) | |
| *A61K 8/60* | (2006.01) | |
| *A61K 8/81* | (2006.01) | |
| *A61K 8/87* | (2006.01) | |
| *A61K 8/891* | (2006.01) | |

(52) U.S. Cl.
CPC ............. *A61K 8/922* (2013.01); *A61K 8/064* (2013.01); *A61K 8/31* (2013.01); *A61K 8/37* (2013.01); *A61K 8/60* (2013.01); *A61K 8/8152* (2013.01); *A61K 8/87* (2013.01); *A61K 8/891* (2013.01); *A61Q 1/10* (2013.01)

(58) Field of Classification Search
CPC ... A61Q 1/00; A61Q 1/02; A61Q 1/04; A61Q 1/10; A61K 8/92; A61K 8/925; A61K 8/064; A61K 8/60; A61K 8/8152; A61K 8/87; A61K 8/31; A61K 8/891
See application file for complete search history.

(56) References Cited

U.S. PATENT DOCUMENTS

| | | | |
|---|---|---|---|
| 5,538,718 A | 7/1996 | Aul et al. | |
| 5,597,849 A | 1/1997 | McGinity et al. | |
| 6,162,421 A | 12/2000 | Ordino et al. | |
| 6,471,951 B1 | 10/2002 | Nardolillo et al. | |
| 8,242,169 B2* | 8/2012 | Yoneda | A61Q 19/00 514/474 |
| 8,323,628 B2* | 12/2012 | Atis | A61K 8/55 424/70.7 |
| 8,920,787 B2* | 12/2014 | Li | A61K 8/8152 424/70.7 |
| 9,744,116 B2 | 8/2017 | L'Oreal | |
| 2004/0265346 A1 | 12/2004 | Verloo et al. | |
| 2005/0118210 A1 | 6/2005 | Kachi et al. | |
| 2005/0191328 A1 | 9/2005 | Taniguchi | |
| 2006/0013792 A1 | 1/2006 | Fontaine et al. | |
| 2010/0266648 A1 | 10/2010 | Ranade et al. | |
| 2014/0102467 A1* | 4/2014 | Pistorio | A61K 8/044 132/202 |
| 2014/0105845 A1 | 4/2014 | L'Oreal | |

FOREIGN PATENT DOCUMENTS

| | | |
|---|---|---|
| CN | 103655386 A | 3/2014 |
| DE | 4128748 A1 | 3/1993 |
| EP | 2314280 | 4/2011 |
| FR | 2873019 A1 | 1/2006 |
| JP | H11505543 A | 5/1999 |
| JP | 2004203788 A | 7/2004 |
| JP | 2007523199 A | 9/2005 |
| JP | 2006028184 A | 2/2006 |
| JP | 2011507865 A | 3/2011 |
| KR | 1020040081457 A | 9/2004 |
| WO | 9636308 | 11/1996 |

OTHER PUBLICATIONS

European Patent Office, International Search Report for International Application No. PCT/EP2017/084769, dated Mar. 7, 2018.

* cited by examiner

*Primary Examiner* — Jyothsna A Venkat
(74) *Attorney, Agent, or Firm* — Bradley Arant Boult Cummings; Timothy L. Capria; Alexandra C. Lynn

(57) ABSTRACT

A process for the production of a solid cosmetic preparation is described wherein a wax phase comprising at least one wax, at least one oil, and if applicable, oil-soluble ingredients and solvents are melted, the molten wax phase is mixed with an aqueous phase comprising at least one water-soluble or water-soluble water-dispersible film former and with a w/o emulsifying system until an emulsion is formed, and the resulting emulsion is allowed to cool to form a wax matrix with aqueous phase droplets embedded therein, and the products made therefrom and their use.

2 Claims, No Drawings

PROCESS FOR PRODUCING A WAX PREPARATION

The invention relates to a process for the production of a cosmetic preparation with a structured wax matrix, the preparation prepared therewith, and its use.

Cosmetic preparations for making up the skin or semi-mucous membranes are commonly known. Such preparations are available in liquid and solid form. Solid preparations are known in the form of makeup pencils, as soft pastes, or in the form of loose or pressed powders. Mixtures of vegetable, animal, or synthetic oils, fats, and waxes that are anhydrous and in which pigments, pearlescing agents, or other effect substances and fillers are dispersed are often used for makeup pencils or pastes. Powders are often made into pressed powder, the powder then being a mixture of pigments, pearlescing agents, or other effect substances and fillers with an oil- or emulsion-based binder that is added to make them easier to handle and process. Also well-known are lipstick masses, i.e. cosmetic preparations in the form of a soft paste that can be applied to the lips. Lipstick masses are usually based on a mixture containing wax and oil to which pigments are added.

General requirements of compositions in the field of decorative cosmetics are simple application, a pleasant feel when applied to the skin, mucous membrane, or semi-mucous membrane, long adherence to the applied location, and no smearing or migration in wrinkles. In addition, the mass must have a long shelf life.

Many known preparations have the disadvantage that they do not adhere well to the applied location and can be easily transferred to materials with which they come into contact, such as dishes, cutlery, glass, textiles, or skin. On the one hand this is unaesthetic, and on the other hand, it requires that applied films or lines be improved. Another problem with preparations containing lipid is that lipophilic substances, especially oils, spread on the skin and on semi-mucous membranes and cause the mass to migrate away from the applied location, and in particular, to migrate into the fine folds of the skin around the lips or eyes. This creates unsightly, unwelcome structures. Skin sebum and perspiration can cause or intensify these effects.

In the case of preparations applied in the region of the eye, such as eyeliner, eyeshadow, or mascara, a "touch-up" is also a problem. Touch-up refers to the phenomenon that some of the applied mass, such as eyeliner or eyeshadow moves due to the movement of the eyelids and the effect of sebum, especially in the wrinkles of the eyelid, producing strip-shaped structures are generated.

To avoid these disadvantages of compositions containing lipid, attempts have already been made to develop preparations that contain no oils, fats, and waxes, and instead are based on dispersions containing polymers in an aqueous or aqueous-alcoholic phase. These dispersions can then form elastic films on the skin or semi-mucous membrane. However, either these films are often more or less water-resistant and then not so pleasant on the skin or they are good to apply and pleasant on the skin, but then not water-resistant.

Emulsions are also known to be used for cosmetic preparations. Since regular wax masses are often very water-resistant but are not resistant to greasy and oily components, whereas water-based cosmetics are often resistant to oils and fats but have poor water resistance, and emulsifiers promote the miscibility of water and oil, emulsions often do not provide satisfactory durability. The durability of emulsions is particularly inadequate when they come into contact with water or endogenous fluids, such as sweat or sebum.

The ability to provide cosmetic preparations that are applied to the eye is particularly demanding. On the one hand, the eye area is particularly sensitive. On the other hand, the durability requirements are particularly high, since both water resistance and lipid resistance are required. Therefore, makeup pencils to be applied to the eye must not be hard and the abrasion must be sufficient. On the other hand, makeup pencils that are too soft and have too much output cannot be applied well and tend to smudge.

Preparations applied to the eye area are also known. In particular, there is a variety of mascara compositions, i.e. compositions that are applied to the eyelashes and usually color them black. For example, US 2015/0079016 describes a mascara composition containing a liquid lipid substance, an emulsifying system, and a film former. Wax may also be present, but should preferably be avoided or, if present, used only in a very small proportion. The finished composition is an o/w emulsion that is fluid and produces a creamy texture.

Furthermore, US 2014/0105845 mentions a wax-based mascara composition that has a wax dispersion with wax particles in the μm range and a latex film former as essential ingredients. The addition of the latex film former is intended to improve the removability of the composition.

Although many different compositions for the preparation of cosmetic products have also been described, especially for use on the eye, a completely satisfactory solution has not yet been found. Compositions in the form of a makeup pencil for application to the eye are often either water-resistant and can then spread due to their lipophilicity or are lipid resistant and are then blurred by the tear fluid. Often compositions in the form of a makeup pencil cannot be applied so well to the eye because the release properties are not optimal.

Frequently, lipid-like ingredients dissolved in solvent that form a layer of lipids after application by evaporation of the solvent are used for such preparations. Here as well, there are limitations with regard to the solvents to be used on the eye, because they must not irritate the eye when evaporating.

The object of the invention was to provide a solid preparation to be applied to the eye, in particular a preparation that may be in the form of a makeup pencil and that is easy and comfortable to apply, is smudge-, water-, and oil-resistant after application, and forms an esthetic, homogeneous colored line. Another object is to provide a preparation that has the lowest possible proportion of lipophilic substances. The mass should have a structure that can be used as a solid freestanding pencil lead or as a pencil lead in a makeup pencil.

In addition, the applied film or the applied line should remain stable on the applied location without migrating or forming stripes on the eyelids.

In order to stabilize the applied composition on the application location, film-forming polymers that leave a permanent film after evaporation of the volatile substances are frequently used. This film should be water-resistant, oil-resistant, and smudge-resistant.

According to the present invention, a process is now provided to produce a preparation that solves the aforementioned problems. The preparation obtained according to the present invention is characterized in that it is easy to apply, adheres to the applied location for a very long time without migrating into the wrinkles, is easy to produce, and is easy to apply because the mass can be shaped as a pencil lead. In addition, both the application and the film that is produced during the application are very pleasant and do not irritate. The film that is produced is water-resistant, oil-resistant, and smudge-resistant. In other words, the preparation according to the present invention produces a film with very high durability that is not dissolved by fats and oils, nor by water. In addition, the preparation according to the present invention is characterized by the fact that it does not contain any ingredients that may irritate the eye; in particular, organic solvents are required only in a very small amount. It can be applied to the skin and semi-mucous membranes.

The preparation according to the present invention is obtained by means of a special process that forms a mass with a special structure. The wax preparation according to the present invention is in solid form, "solid" here meaning that the wax preparation is not fluid at room temperature under the effect of its own weight.

It has surprisingly been found that it is possible with the process according to the present invention to produce a wax preparation that can be applied softly and pleasantly, is also very pleasant on the skin and the semi-mucous membrane after application, and nevertheless adheres very well.

The invention therefore provides a process for producing a solid cosmetic preparation wherein a) a wax phase comprising at least one wax, at least one oil, and if applicable, oil-soluble ingredients is melted, b) a molten wax phase is mixed with an aqueous phase, containing at least one water-soluble and/or water-dispersible film former, and a w/o emulsifying system to form an emulsion, and c) the resulting emulsion is allowed to cool to form a wax matrix having aqueous-phase droplets embedded therein.

The process according to the present invention makes it possible to provide a preparation with a structure that solves the problems outlined above. The wax matrix formed by the process with the droplets embedded therein is mechanically very stable and may be processed to form freestanding pencil leads or pencil leads that can be inserted into sleeve blanks. The outer wax layer allows the preparation to remain very stable. Embedded in the wax matrix are droplets that contain an aqueous phase with a film former dissolved or dispersed therein, and that do not merge or disappear. In the application, a layer of wax is applied to the skin and the water droplets migrate outward, forming a layer over the wax layer, evaporating the water, and leaving a film overlying the wax layer. As a result, the applied layer remains stable on the applied location. If pigments are included, the wax layer keeps the pigments embedded in the formed structure so that the pigments also remain on the applied location without migrating away or being carried away. The film former protects the wax layer from spreading or migrating. This produces a very high degree of durability.

This special structure is formed only when the process according to the present invention is carried out in the three stages indicated. Briefly, a water-in-oil emulsion is formed from the molten wax phase and film-forming aqueous phase which on cooling forms a matrix of solid wax and water droplets dispersed therein.

In stage a), a fluid wax phase is formed. To this end, at least one wax is melted and hydrophobic ingredients, such as oil and oil-soluble ingredients, are added. If pigments and/or soluble dyes are used, they may also be added in stage a).

Any cosmetically acceptable wax is suitable. The appropriate waxes are well-known to specialists. Examples are waxes of natural origin, such as beeswax, carnauba wax, candelilla wax, ouricury wax, Japan wax, paraffin wax, microcrystalline wax, lanolin wax, montan wax, ozokerite, and hydrogenated oils, such as hydrogenated jojoba oil. Waxes of synthetic origin, such as polyethylene waxes, Fischer-Tropsch waxes, and silicone waxes, are also suitable.

You can use just one kind of wax or a mixture of waxes; the selection is made based on the desired consistency of the finished composition among other factors. In the preparation according to the present invention, a mixture of different waxes, such as a mixture of waxes with different melting points and/or a mixture of different natural and/or synthetic waxes, is preferred. It has been found that especially a mixture of one or more vegetable waxes and different Fischer-Tropsch waxes with different melting points produces very good results. Mixing two or more different waxes produces a homogeneous mixture for which the desired melting point can be set very precisely.

The melting point of the wax component is important for the application and wear properties. If the melting point is too high, it is difficult to formulate a mass that can be applied. In this case, a high proportion of oily ingredients must be added, which in turn adversely affects the stability of the preparation on the applied location. On the other hand, if the melting point is too low, the wax will soften and smear on the applied location. In addition, the shelf life is also limited. Since the composition is applied to the skin and semi-mucous membrane of the eye, the melting point of the wax component should be above 50° C. in any case.

Particularly suitable is a combination of a high-melting wax, e.g. a wax with a melting point from 80° C. to 85° C., a mid-range melting wax, e.g. a wax with a melting point in a range from 65° C. to 80° C., and a low-melting wax, e.g. a wax with a melting point in a range from 55 to 60° C. Suitable waxes are Fischer-Tropsch waxes, which are available with many different melting points, and vegetable waxes, such as candelilla wax, so that the right combination can be found for each application.

The wax or the waxes are present in the composition in a proportion necessary to form a matrix. Suitable amounts are in a range from 5% to a percent by mass, preferably from 8% to a percent by mass, for example, up to 13% by mass. Each indication in % by mass refers to the finished composition, unless otherwise indicated.

If several waxes are included, their amount is adjusted according to the desired melting point and other desired properties, as is known to specialists. For example, a wax phase may comprise up to about the percent by mass of a high-melting wax, about 40% of a mid-range melting wax, and about 40% to about 70% by mass of a low-melting wax.

The wax phase also contains at least one oil that serves to soften and/or dissolve the wax.

Both volatile and nonvolatile oils as well as a mixture of both may be used. It has been shown to be advantageous to use at least one nonvolatile oil to make and keep the wax supple as well as at least a small proportion of a volatile oil to make the composition easier to apply, in which case the volatile oil evaporates after application and leaves the wax in the desired structure.

The nonvolatile oil can be a polar or an apolar oil. Examples of apolar oils are especially silicone oils, such as linear and cyclic polydimethylsiloxanes, which are liquid at room temperature. Suitable silicone oils can dissolve waxes and allow for a smooth application of the preparation.

Nonvolatile oils that are also suitable for the preparation according to the present invention are polar oils, such as those of synthetic or mineral origin, which in addition may also contribute additional properties, such as plasticizers, for example. Examples of oils that are commonly used in cosmetic compositions include triglyceride oils derived from plants, such as wheat germ oil, corn oil, sunflower oil, or oils from other plants that contribute useful properties. Synthetic oils, such as esters of myristic acid like isopropyl myristate, palmitic acid, stearic acid, etc., as well as nonvolatile hydrocarbons of synthetic and mineral origin, such as isoparaffins and paraffin oils are suitable. Another example of a nonvolatile oil that can increase the suppleness of the waxes, improve pigment wetting, and make the application more comfortable is butylene glycol cocoate.

The wax phase of the preparation according to the present invention may contain at least one polar or one apolar oil, or a mixture of polar and apolar oils.

Volatile hydrocarbons, such as isododecane or volatile silicone oils, such as a volatile dimethicone with a viscosity of 1.5 cSt, available as silicone fluid 1.5 cSt, may be used as the volatile oil. The volatile oil contributes to the flexibility and suppleness of the mass and aids in wetting the particulate ingredients. In addition, it also helps the film formed after application to dry faster.

The oil or oils are present in an amount that is sufficient to make the wax supple or dissolve. Suitable amounts are in a range from about 2% to about 10% percentage by mass, preferably from about 3% to about 8% by mass. When both volatile and nonvolatile oils are included, the ratio of nonvolatile oils to volatile oils usually ranges from about 10:1 to about 1:2.

It has been found that a preparation that has less than 30% wax phase and is nevertheless very stable can be produced with the ingredients according to the present invention. Thus, in one embodiment, the entire composition has less than 30% percent by mass of the wax phase, wherein the wax phase is as defined above or in the claims. The wax phase has lipophilic ingredients; as a rule, all lipophilic ingredients are present in the wax phase.

If the preparation is to contain particulate ingredients, they may be added either in stage a) or stage b). Usually they are added to the molten wax. Particles containing active ingredients such as colorants, effect substances, and also functional components, can be added as particulate materials. Since the composition produced according to the present invention is to be used in decorative cosmetics, usually at least one colorant, such as pigment and/or colorant is included. If present, pigments are added in the amount required to produce the desired coloration. It can be one pigment or a mixture of two or more pigments. Depending on the desired coloration, the pigment portion can be from 8% to 30% by mass, preferable up to 28% by mass. Special effect substances, such as light-diffusing pigments or colored fluorescent or luminous, glittering particles, may also be included instead of or in addition to the pigments. They may be present in a proportion of up to 10% by mass, preferably up to 5% by mass. Unless otherwise indicated, the percentages described here generally refer to the total amount of the preparation.

Of the colorants suitable for the composition according to the invention, mention may be made, by way of example, of pigments such as titanium dioxide (C.I. no. 77891), iron oxides (C.I. no. 77491, 77492, 77499), ultramarine (C.I. no. 77007), Berlin blue/ferric blue (C.I. no. 77510), carbon black (C.I. no. 77267) chrome oxide green (C.I. no. 77288), chromium oxide hydrate green 5 (C.I. no. 77289), manganese violet (C.I. no. 77742), zinc oxide (C.I. no. 77947), barium sulfate (C.I. no. 77120), bismuth oxychloride, glitter such as mica, which may be at least partially coated with colorants such as titanium dioxide (C.I. no. 77891) and/or with other metal oxides such as iron oxides, chromium oxide green, chromium oxide hydrate green, ultramarine, bismuth oxychloride (C.I. no. 77163); platelet-shaped, if applicable, finely divided metal powders, such as aluminum (C.I. no. 77000), copper (C.I. no. 77400), bronze (C.I. no. 77400), brass (C.I. no. 77400), silver (C.I. no. 77820) or gold (C.I. no. 77480); organic colorants which have been suitably rendered insoluble by varnishing, e.g. complex salts of carminic acid (C.I. no. 75470) varnishes of fluoresceins, monoazo dyes, bisazo dyes, indigotine dyes, pyrazole dyes, quinoline dyes, triphenylmethane dyes, anthraquinone dyes, and xanthan dyes. Examples of these are FD&C red no. 3 (C.I. no. 45430), D&C red no. 6 (C.I. no. 15850), D&C red no. 7 (C.I. no. 15850:1), D&C red no. 21 (C.I. no. 45380:2), D&C red no. 22 (C.I. no. 45380), D&C red 27 (C.I. no. 45410:1), D&C red 28 (C.I. no. 45410), D&C red 30 (C.I. no. 73630), D&C red no. 33 (C.I. no. 17200), D&C red no. 34 (C.I. no. 15880:1), FD&C yellow no. 5, (C.I. no. 19140), FD&C no. 7 (C.I. no. 45350:1), D&C yellow no. 10 (C.I. no. 47005), D&C orange no. 5 (C.I. no. 45370:1), D&C orange no. 10 (C.I. no. 45425:1), FD&C green no. 3 (C.I. no. 42053), D&C green no. 5 (C.I. no. 61570), D&C green no. 6 (C.I. no. 61565), FD&C blue no. 1 (C.I. no. 42090), D&C violet no. 2 (C.I. no. 60725). Further suitable pigments are boron nitrides, both platelet-shaped and spherical polymer particles, and silica particles, which in turn may be mixed, loaded, or coated with the aforementioned colorants. Other examples are light-diffusing pigments (LDP) or fluorescent particles.

Pigments that are especially preferred are selected from iron oxides, titanium dioxide, zinc oxide, carbon black, carmine, ferric ferrocyanide, chromium hydroxide green, chromium oxide green, manganese violet, ultramarine blue and yellow 5, as these have a particularly good color coverage and allow the production of most mixed colors.

An active ingredient that has an effect on the environment of the application location may be included as a functional component, either in addition to or instead of the colorant. Because the preparation is applied in the eye area, it can contain components such as those that fill in wrinkles around the eyes and/or firm and tighten the skin to make it look younger. The wrinkles can be filled either by pigments, especially LDP, or can be affected by absorbing hyaluronic acid and/or their derivatives. Active ingredients that are usually used for this purpose, such as collagen, ingredients that increase collagen synthesis, such as *Ginkgo biloba* and *ginkgo* extracts, vitamin C, or creatine, are also suitable to be added to the preparation according to the present invention. UV filter substances that protect the sensitive skin around the eyes from UV rays can also be added in a conventional manner and in the conventional amounts. Active ingredients that have an influence on dry eyelids or dry eyes can also be included in the preparation.

The wax phase in molten form is obtained either by melting the wax and adding oil and other hydrophobic or oil-soluble components, or by melting wax and oil together and adding additional oil-soluble ingredients if necessary. Pigments and/or oil-soluble colorants can also be added to the wax at the beginning, added to the wax melt, or added together with the aqueous phase. Usually, pigments and oil-soluble colorants are added to the wax melt.

The melting is done in a customary manner. The wax phase is heated to a temperature from approximately 50° C. to approximately 90° C., preferably 60° C. to 85° C., particularly preferably 70° C. to 80° C., so that the wax phase with wax and other ingredients, if applicable, is in fluid form. Additional components of the wax phase can then be added to the molten wax. Ideally, the wax phase will have a temperature in a range from about 50° C. to about 90° C., preferably 65° C. to 80° C. for further processing.

The temperature of the wax phase depends on the melting point of the waxes used, among other factors. In any case, the temperature must be high enough for all wax to be in a molten form. On the other hand, the temperature of the wax phase must not be too high, especially not above 100° C., otherwise the water will evaporate when the aqueous phase is added. Therefore, a suitable range is from about 50° C. to about 90° C., preferably 60° C. to 85° C., particularly preferably 70° C. to 80° C.

In stage b), the molten wax phase is mixed with an aqueous phase to form an emulsion. For this purpose, an aqueous phase is formed consisting of water, a hydrophilic film former, and water-soluble ingredients, if applicable. The hydrophilic film former can be a water-soluble or water-dispersible film former. The terms "dispersed" and "dissolved" are used equivalently in conjunction with polymers. Because the transitions between dispersion and solution for polymers often cannot be determined, polymer dispersion is understood to mean a composition in which the polymer is compatible with the solvent, does not settle, and therefore is dissolved and/or dispersed, and does not separate.

More precisely, a hydrophilic film former is a polymer that is compatible with water, i.e. it can be dispersed or dissolved in an aqueous medium, such as water or an aqueous solvent, and forms a film after application. The aqueous medium is usually water, but can also be a mixture of water with water-soluble solvents, such as alcohol. Preferably, the aqueous medium should consist of water.

At least one water-soluble or water-dispersible polymer or copolymer that can form a film is contained in the aqueous phase as the hydrophilic film former. A hydrophilic film former or a combination of two or more hydrophilic film formers can be used for the preparation according to the present invention. The suitable film formers are known to specialists and can be selected in a customary manner. Examples of suitable hydrophilic film formers are polymers and copolymers containing acrylic and polyurethanes, such as copolymers of styrene, acrylates and ammonium methacrylates, polymers and copolymers based on polyurethane, or combinations thereof. Examples of suitable hydrophilic film formers are polyurethane and styrene/acrylates/ammonium methacrylate copolymers.

Hydrophilic film-forming polymers are typically available as an aqueous dispersion, for example, with a polymer content 30% up to about 70% by mass, such as 40% to 60% by mass. Unless otherwise indicated, when an amount of film-forming polymer is indicated, the term refers to the polymer itself and not the amount of dispersion.

The proportion of hydrophilic film-forming polymer as a whole used for the preparation of the present invention is in a range from 8% to 25% by mass (parts by mass of polymer per part of mass of the finished preparation). For example, if both polyurethane polymer and polymer containing acrylic are used, the ratio of polyurethane polymer to the polymer containing acrylic can be in a range from 4:1 to 1:4.

In addition, water-soluble and/or water-compatible ingredients, such as excipients, or other agents can be added to the aqueous phase to support the desired properties. Examples are preservatives, such as phenoxyethanol, and boosters, such as caprylyl glycol or propanediol. Emollients or humectants, such as glycerine and butylene glycol, may also be used. They are used to make the skin supple and keep it moisturized. Emollients like butylene glycol also serve to increase the flexibility and elasticity of aqueous film formers. Therefore, according to the present invention, humectants such as glycerin and butylene glycol are preferably used in conventional amounts such as a proportion from 4% to 8% by mass.

When a water-soluble dye is used in the preparation, either in addition to a pigment and/or oil-soluble colorant, or as the sole colorant, it becomes part of the aqueous phase. A water-soluble colorant may be added either to the aqueous phase prior to blending with the fat phase or during emulsification.

The preparation of the aqueous phase, i.e., the mixing of film formers and other ingredients of the aqueous phase can be done at room temperature, or the aqueous phase can be heated to dissolve other water-soluble ingredients more easily. In one embodiment, the aqueous phase is heated to approximately the temperature of the wax phase.

Stage b) consists of mixing the molten wax phase with the aqueous phase to form a w/o emulsion, which then produces the desired structure upon cooling. Preferably, the aqueous phase is heated to prevent wax from solidifying as the phases are mixed together. A temperature at or above which the wax melts is suitable. A temperature of about 100° C. or higher is not suitable because it will cause the aqueous phase to evaporate. A temperature range from about 50° C. to about 90° C., particularly 60° C. to 85° C. has been found to be favorable. In other words, in one embodiment, the aqueous phase is heated to a temperature in a range from about 50° C. to about 90° C., particularly 60° C. to 85° C., before being mixed with the wax phase.

To aid in the formation of a w/o emulsion, at least one w/o emulsifying system is added. A w/o emulsifying system comprises at least one w/o emulsifier or a combination of two or more w/o emulsifiers. It is also possible to use a mixture of different emulsifiers, such as a combination of w/o and o/w emulsifiers or emulsifying systems. The w/o emulsifying system is a combination of at least one emulsifier, and if applicable, additional coemulsifiers or reinforcing, supporting, or interacting compounds, wherein the system as a whole promotes the formation of a w/o emulsion. Examples of emulsifiers that are well suited for the process according to the present invention are sucrose esters, especially those of fatty acid, such as those containing at least 6 carbon atoms, like 6-24 carbon atoms, or emulsifiers based on polyglyceryl fatty acid esters, or mixtures thereof. It has been found that an emulsifying system well suited to the present invention is a combination of at least one sucrose ester and at least one emulsifier based on polyglyceryl fatty acid ester. This system has proved to be very stable regardless of the amount of pigments and fillers, so that preparations with high pigment and/or filler content can also be produced with this emulsifying system.

Examples of suitable sucrose esters are sucrose laurate, sucrose stearate, sucrose distearate, and sucrose polystearate. Examples of emulsifiers based on polyglyceryl fatty acid ester are polyglyceryl mono fatty acid esters, polyglyceryl difatty acid esters, or polyglyceryl oligo fatty acid esters. The fatty acid may be a saturated, monosaturated, or polyunsaturated fatty acid, such as one with 14 to 20 carbon atoms. Examples of these are (identified by INCI names): Polyglyceryl-5 dioleates, polyglyceryl-10 diisostearates, polyglyceryl-6 distearates. The most suitable emulsifier in each case can be determined easily by the specialist; for example, it may be advantageous to use emulsifiers with the lowest possible HLB value. In this case, those esters having more than one fatty acid residue are preferred because the higher the degree of esterification, the lower the HLB value.

Additional stabilizing agents for the emulsion can be used in combination with the w/o emulsifier according to the present invention or as part of the w/o emulsifying system.

The emulsifier or emulsifying system can be added either to the wax phase or the aqueous phase, or the wax phase can first be mixed with the aqueous phase and then the emulsifier or emulsifying system can be added. When several emulsifiers or one emulsifier and one coemulsifier are used, each of these components may be added to each phase or mixture. Usually, the emulsifier or emulsifying system is worked into the molten wax phase, for example, melted together with the wax or added to the molten wax phase, and only then added the water phase.

The mass fraction percentage of the emulsifier of emulsifying system in the total composition of the preparation according to the present invention is 1% to 10% by mass, preferably 1.5% to 7.5% by mass, particularly preferably 3% to 6% by mass. The exact mass fraction percentage of the emulsifier depends on the chemical nature of the other components and the emulsifier used in each case. A specialist can determine the most suitable amount in each case in simple routine tests. If too small an amount of emulsifier is used, no homogeneous emulsification takes place.

To form an emulsion of wax phase and aqueous phase, the molten wax phase and the aqueous phase are mixed together with the w/o emulsifier or w/o emulsifying system. The emulsifier or emulsifying system can either be added to at least one of the two phases before mixing or to a mixture of the two phases before emulsification. As a rule, the emulsifier, for example, the w/o emulsifier or w/o emulsifying system, is mixed with the wax phase before, during, or after the melting.

Conventional devices that are commonly used to produce emulsions as well as cosmetic masses may be used to mix the phases. One example of a suitable device is a rotor-stator device, such as the machine that is commercially available under the name Turrax or Ultraturrax.

Both phases are mixed at a higher temperature in a range from about 50° C. to 90° C. until a homogeneous composition is produced. In other words, the mixing is done while the mixture is heated. Preferably, the mixing temperature is 60° C. to 80° C., particularly preferably 70° C. to 80° C. The mixing is done for a period of time until the desired emulsion is produced. This is usually after 1 to 20 minutes, particularly 2 to 15 minutes, for example, 5 minutes to 10 minutes.

Mixing produces a w/o emulsion of the wax phase and aqueous phase. This is important in order to produce the later structure of the preparation according to the present invention, a wax phase as a continuous phase, and an aqueous phase as a discontinuous phase. The emulsion has a molten wax phase consisting at least of wax and oil and oil-soluble portions as a continuous phase. Droplets of the aqueous phase consisting at least of water and a dissolved/dispersed film former are distributed therein. This way, the film former is distributed finely in dissolved or dispersed form in the wax phase. Upon cooling, the wax phase solidifies and forms a matrix for the droplets of the aqueous phase as a continuous phase.

In addition to the essential components described above, additional additives and excipients common in cosmetics, such as fillers, plasticizers, preservatives, perfume, and others, may be added to the preparation. These substances can either be added to each compatible phase prior to mixing, added to a mixture of the two phases before, during, or after the emulsification, or added to the emulsion while it is still warm and especially fluid. In particular, sensitive additives, such as scents or perfume, may be added at the end of the mixing period to minimize the temperature stress.

Fillers serve to give the mass the desired structure. Examples are talc, kaolin, bentonite, hectorite, montmorillonite, cerium oxide, silicon oxide, boron nitride, nylon powder, polyethylene powder, polypropylene powder, silk powder and mixtures thereof, polyvalent metal soaps, non-swellable starches, natural and synthetic peeling bodies, sand, bran products, algae derivatives, thermosets, thermoplastics, elastomers, and mixtures as well as hybrids of the ingredients listed. If fillers are added to the preparation according to the present invention, they are used in the conventional amounts.

Furthermore, the preparation according to the present invention may contain at least one humectant. Suitable humectants are monohydric and polyhydric alcohols, urea derivatives, or vegetable extracts. Examples of these are butylene glycol, polyhydric alcohols and their esters, such as glycerol, diglycerol, triglycerol, diethylene glycols, amyl alcohol, hexanediol, pentaerythritol, sorbitol, xylitol, mannitol and alditol, sucrose, laureth-2 benzoate, ethylhexyl sebacate, citric acid esters such as tributyl citrate, synthetic short-chain esters, pentaerythrityl esters and oligo pentaerythrityl esters. Skin moisture can be preserved better with such moisturizers in the composition. This makes the skin look fuller and smoother.

If humectants are added to the composition of the present invention, they can be used in the usual amount. A proportion in a range from 1% to 15% by mass, preferably 2% 10% by mass, and particularly preferably 3% to 8% by mass, based on the total preparation, is suitable.

The preparation according to the present invention can contain preservatives in the usual amounts. All preservatives known to specialists in the cosmetic field are suitable here. One example of this is phenoxyethanol, which is used in a known amount.

The emulsion produced in stage b) is then allowed to cool in stage c) to produce a wax matrix with embedded droplets from the aqueous phase. The cooling is done in a customary manner. Shock cooling is possible, but it is also possible to pour the composition into containers and to allow them to cool at ambient temperature. In one embodiment, the emulsion is poured into a mold, such as a pencil lead mold or sleeve blank and allowed to cool. If necessary, the mold can be tempered so that the emulsion can fill out the mold and cool slowly.

As already explained above, the preparation according to the present invention is formed as it cools with an advantageous structure, namely a wax matrix, in which droplets with film formers are distributed homogeneously. After cooling, when the wax matrix solidifies, the droplets can no longer change. They are "trapped in the matrix", so to speak. Because the water droplets and the wax matrix are not very compatible with each other, the droplets do not change; in particular, a confluence of several droplets separated by wax matrix is prevented.

The mass obtained after cooling is so stable that it can be used in a variety of forms. In particular, pencil leads can be cast from the emulsion that are so stable that they can be used as freestanding pencil leads, as in an applicator, as well as pencil leads that can be inserted in a sleeve blank. The preparation according to the present invention can then be applied in the form of a makeup pencil. Other forms of the preparation according to the present invention are also possible. But here the form of a makeup pencil is best suited for application.

The invention further relates to a pencil lead for a makeup pencil, especially an eyeliner, comprising the wax preparation according to the present invention. After cooling, the wax preparation according to the present invention is poured into a pencil lead mold to form the emulsion. The resulting pencil lead is so firm that it can either be inserted into a sleeve blank or used freestanding in an applicator. A pencil has an outer part and a core, wherein the outer part forms a shell, which encompasses the core. Based on current technology, the shell can be made of wood, plastic, or metal. In order to avoid premature evaporation of the solvent, the pencil should preferably have a sealed cap and a thick protector to prevent the solvent from escaping.

The wax preparation according to the present invention is very well suited for use on the eye. It is easy to apply and dries quickly. It does not irritate and does not run. The resulting homogeneous film adheres very well, does not migrate away, does not smear, and is resistant to friction. Due to the fast drying, touch-up is not necessary.

The preparation according to the present invention is described based on the following example, which, however, is not intended to be exhaustive. Where applicable, the raw materials are indicated with their INCI. Unless otherwise indicated, the information on their mass (in % by mass) is based on the total mass of the preparation.

EXAMPLE

A preparation that is suitable as a pencil lead mass was produced. The ingredients are indicated in the following table, the amounts in each case being the % by mass (mass relative to the total composition).

Phase A

| | |
|---|---|
| Black pigment CI77499 | 18.13 |
| *Euphorbia cerifera* wax | 3.63 |
| Synthetic wax schmp. | 1.81 |
| Synthetic wax schmp. | 7.25 |
| Polyglyceryl-5 dioleate | 2.72 |
| Sucrose polystearate | 2.72 |
| Dimethicone | 3.63 |
| Butylene glycol cocoate | 0.91 |

Phase B

| | |
|---|---|
| Aqua | 38.24 |
| Butylene glycol | 6.35 |
| Phenoxyethanol | 0.50 |
| Tris(hydroxymethyl)aminomethane | 0.68 |
| Polyurethane 35 | 3.36 |
| Styrene/acrylates/ammonium Methacrylate copolymer | 10.07 |

To produce the preparation, *euphorbia* cerifera wax and the two synthetic waxes were mixed with dimethicone, then the oil butylene glycol cocoate followed by polyglycerol 5 dioleate, and sucrose polystearate were added as emulsifiers, and the resulting mass was heated to produce a molten wax phase. The molten mass was then homogenized with the black pigment. This produced wax phase A. Then polyurethane and styrene/acrylates/ammonium methacrylate copolymer were mixed together, each as a 40% aqueous dispersion, and phenoxyethanol was added as a preservative. Tris(hydroxymethyl)aminomethane was also added to adjust the pH. The aqueous phase was then heated to a temperature of about 70° C. and the wax phase, which has a temperature in a range from 85° C. to 95° C., was added slowly with constant stirring. In order to form a stable and homogeneous emulsion, the mixture was homogenized in a sealed system by a dispersing disk for a while, keeping the temperature of the mixture in a range from 85° C. to 95° C. Next, the molten mass was poured into a casting mask to form a pencil lead and allowed to cool at room temperature.

After cooling, a pencil lead was produced that could be placed in a makeup pencil and used as an eyeliner.

With the eyeliner lead produced in this manner, a black line was drawn around the eyes of test subjects and the appearance was tested immediately after application and six hours later. This produced a strongly covering, very homogeneous line that had practically not changed after six hours.

The application of the eyeliner was perceived by the test subject as very pleasant. The eyeliner line remained in place, required no touch-up, and did not migrate into the wrinkles. After drying, the test subject rubbed across the line, and the line practically did not change.

The invention claimed is:

1. A wax preparation, comprising:
a continuous wax phase comprising at least one wax; and
2%-10% of a volatile silicone oil; and
1%-10% of a water-in-oil emulsifying system,
wherein the water-in-oil emulsifying system comprises: a sucrose ester-based emulsifier selected from the group consisting of sucrose laurate, sucrose stearate, sucrose distearate, sucrose polystearate, and combinations thereof, and
a polyglyceryl fatty acid ester-based emulsifier selected from the group consisting of a polyglyceryl-5 dioleate, polyglyceryl-10 diisostearate, polyglyceryl-6 distearate, and combinations thereof; and
a discontinuous aqueous phase comprising water and 8%-25% film former, wherein the film former is a mixture of polyurethane 35 and styrene/acrylates/ammonium methacrylate copolymer.

2. A pencil lead for a pencil, comprising:
a solid-form preparation, wherein the solid-form preparation comprises
a continuous wax phase comprising at least one wax; and
2%-10% of a volatile silicone oil; and
1%-10% of a water-in-oil emulsifying system,
wherein the water-in-oil emulsifying system comprises: a sucrose ester-based emulsifier selected from the group consisting of sucrose laurate, sucrose stearate, sucrose distearate, sucrose polystearate, and combinations thereof, and
a polyglyceryl fatty acid ester-based emulsifier selected from the group consisting of a polyglyceryl-5 dioleate, polyglyceryl-10 diisostearate, polyglyceryl-6 distearate, and combinations thereof; and
a discontinuous aqueous phase comprising water and 8%-25% film former, wherein the film former is a mixture of polyurethane 35 and styrene/acrylates/ammonium methacrylate copolymer.

* * * * *